(12) United States Patent
Furuya et al.

(10) Patent No.: US 6,768,018 B2
(45) Date of Patent: Jul. 27, 2004

(54) PREPARATION OF ORGANOHALOSILANES

(75) Inventors: Masaaki Furuya, Tokyo (JP); Hajime Ishizaka, Annaka (JP); Mikio Aramata, Gunma-ken (JP)

(73) Assignee: Shin Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/716,617

(22) Filed: Nov. 20, 2003

(65) Prior Publication Data

US 2004/0102641 A1 May 27, 2004

(30) Foreign Application Priority Data

Nov. 22, 2002 (JP) ........................................ 2002-338840

(51) Int. Cl.[7] .............................................. C07F 7/04
(52) U.S. Cl. ....................................................... 556/472
(58) Field of Search ........................................ 5556/472

(56) References Cited

U.S. PATENT DOCUMENTS 3,133,109 A 5/1964 Dotson

FOREIGN PATENT DOCUMENTS

| EP | 0 256 876 A2 | 2/1988 |
| JP | 4-59318 B2 | 9/1992 |
| JP | 9-194490 A | 7/1997 |

Primary Examiner—Samuel Barts
(74) Attorney, Agent, or Firm—Birch, Stewart, Kolasch & Birch, LLP

(57) ABSTRACT

When oganohalosilanes are prepared by charging a reactor with a contact mass containing metallic silicon and a copper catalyst, and introducing an organohalide-containing gas feed into the reactor, the partial pressure of organohalide gas in the gas feed is manipulated so as to keep the temperature within the reactor substantially constant. The precise control of reactor internal temperature ensures that organohalosilanes with a higher useful silane content are produced in a safe and inexpensive manner and in high yields from the contact mass having perpetually changing reactivity.

6 Claims, 2 Drawing Sheets

PREPARATION OF ORGANOHALOSILANES

This Nonprovisional application claims priority under 35 U.S.C. § 119(a) on Patent Application No(s). 2002-338840 filed in Japan on Nov. 22, 2002, the entire contents of which are hereby incorporated by reference.

This invention relates to a process for preparing organohalosilanes, and more particularly, to a process for preparing organohalosilanes by industrial direct reaction that can increase the productivity of useful silane in the organohalosilane product.

BACKGROUND OF THE INVENTION

In the industry, organohalosilanes are produced by catalytic reaction of a contact mass of metallic silicon and copper catalyst with organohalides, known as Rochow reaction. In the production of methylchlorosilane, for example, not only dimethyldichlorosilane is formed as the main product, but methyltrichlorosilane, trimethylchlorosilane, methyldichlorosilane and methylchlorodisilanes are also formed as by-products. It is important to raise the yield of dimethyldichlorosilane having the largest demand among these silanes and to increase the reaction rate.

In this reaction, methyltrichlorosilane forms in a large amount next to dimethyldichlorosilane. The ratio in production weight of methyltrichlorosilane (T) to dimethyldichlorosilane (D) is generally indicated by the index T/D. Lower values of T/D are desired. In order to increase both the yield of dimethyldichlorosilane and the reaction rate, a number of engineers have made studies on the catalyst and metallic silicon, the system, the process and operating conditions.

Production of methylchlorosilanes is industrially carried out using fluidized bed reactors. The optimum value of reaction temperature is generally about 300° C. though it varies somewhat with the type of catalyst. Maintaining the reaction temperature at an optimum level is very important to establish a high reaction rate and a high yield of useful silane at the same time. If the reaction temperature is too high, the amount of by-products formed increases. Probable causes include an increased amount of hydrogen group-containing silane presumably resulting from decomposition of methyl chloride, and the deposition of carbon on the contact mass surface and concomitant degradation of the contact mass. On the other hand, if the reaction temperature is too low, the reaction rate becomes slower, and if extremely low, production of dimethyldichlorosilane is also retarded.

On abrupt temperature changes, active sites on the contact mass surface serving as heat generation sources are expected to undergo greater temperature changes than macroscopic temperature readings by a thermocouple. It is then believed that the yield of dimethyldichlorosilane is sensitive to temperature changes within the reactor even if the changes are small. It is thus preferred to minimize the fluctuation of temperature within the reactor throughout the period of organohalosilane production.

Production of methylchlorosilane continues over about ten days to several weeks. During the period, fresh metallic silicon powder and catalyst powder are continuously or discontinuously supplemented as the metallic silicon powder is consumed and as the metallic silicon powder and catalyst powder are carried away from the system along with the fluidizing gas. Then the reactivity of the contact mass does not remain constant during the period and changes at all times under the influence of the properties (particle size, particle size distribution, impurity concentration, etc.) of metallic silicon, the type of catalyst, the properties (particle size, particle size distribution, impurity concentration, etc.) of catalyst, catalyst concentration, impurity concentration and the like. Since the changing reactivity is accompanied by perpetually changing amounts of heat generation, the maintenance of the reaction temperature requires a sophisticated control system. For the safety of production, it is also very important to maintain the temperature within the reactor at a certain value so as to prevent any temperature rise within the reactor.

In the production of methylchlorosilane, a heating operation of heating the contact mass charged to nearly the reaction temperature and a cooling operation following the start of heat generation due to reaction by introduction of methyl chloride are necessary in order to maintain the temperature within the reactor at a certain value. Heating may be carried out by circulating a heat medium oil through a jacket surrounding the reactor and/or an inner coil disposed within the reactor, while direct heating by a heater is also acceptable. Cooling may be carried out by circulating a (cool) heat medium oil through a jacket surrounding the reactor and/or an inner coil disposed within the reactor, while air cooling is also acceptable.

The reaction temperature within the reactor may be maintained at a desired level by manipulating the quantity of cooling. The quantity of cooling may be changed by changing the temperature or flow rate of heat medium or a combination thereof. However, the former means is difficult to maintain a constant temperature because a long time is taken to change the temperature of heat medium oil being circulated, indicating a slow response of temperature control. Still worse, the response becomes delayed as the apparatus becomes of larger size. Also, if the temperature of heat medium is lowered in order to increase the quantity of cooling, the wall temperature of the heat transfer surface becomes lower. Then high-boiling products and metal halide condense thereon, and metallic silicon powder and catalyst powder deposit on such condensates, causing to lower the coefficient of heat transfer.

The latter provides effective temperature control as compared with the former. The latter intends to increase the quantity of cooling by increasing the amount of heat medium oil circulated to thereby increase the coefficient of heat transfer. However, the circulation amount of heat medium oil and the coefficient of heat transfer are not in simple proportion. For example, when the heat medium oil is circulated in laminar flow, the coefficient of heat transfer, which is in proportion to an approximate ⅓ power of a flow velocity, is in proportion to an approximate ⅓ power of the circulation amount. Then, the circulation amount of heat medium and the coefficient of heat transfer are related as shown in FIG. 1. In the low flow rate region, the coefficient of heat transfer is sensitive to changes of circulation amount, but in the high flow rate region, the coefficient of heat transfer changes a little with changes of circulation amount. Then, in order to increase the precision of temperature control, the system must be designed with greater upper limits on the circulation amount of heat medium oil so that the system is operated in the low flow rate region during steady operation. This necessitates an extra capacity cooling unit relative to the cooling capacity for steady operation, increasing the cost of installation.

An auxiliary method of stabilizing temperature control is disclosed in JP-B 4-59318 where an inert solid powder is added to a contact mass containing metallic silicon and copper catalyst for ameliorating the temperature control in the fluidized bed reaction zone. Since the inert solid powder occupies a certain volume within the reactor, the amount of reactants admitted per reactor volume is reduced, resulting in a lower productivity.

U.S. Pat. No. 3,133,109 proposes the use of a heat transfer coil which is disposed as temperature control means in the reaction chamber of a fluidized bed reactor. With only the coil, the control effect is insufficient. JP-A 9-194490 discloses a method for preparing organohalosilanes at a high selectivity and in high yields by setting the product of a density by a linear velocity of organohalide-containing gas feed within a selected range. This method requires complicated management.

As discussed above, the prior art methods have problems including poor temperature control (response or stability), increased installation costs, and low productivity.

SUMMARY OF THE INVENTION

An object of the present invention is to provide a method for preparing organohalosilanes while keeping a certain temperature within the reactor to maintain a high productivity of useful silane, whereby organohalosilanes are produced at a low cost.

It has been found that by manipulating the partial pressure of organohalide gas in a gas feed to a reactor for organohalosilane production, the temperature within the reactor is maintained at a substantially constant appropriate level during the organohalosilane-forming reaction. Specifically, by manipulating the partial pressure of organohalide gas as one reactant to change the amount of heat generation due to reaction, the temperature within the reactor can be held at an appropriate level with a very high precision. The productivity of useful silane is maintained high. As a result, organohalosilanes are produced at a low cost.

Accordingly, the present invention provides a process for preparing oganohalosilanes comprising the steps of charging a reactor with a contact mass containing metallic silicon particles and a copper catalyst, and introducing an organohalide-containing gas feed into the reactor to effect reaction to form organohalosilanes, wherein the partial pressure of organohalide gas in the gas feed is manipulated so as to keep a substantially constant temperature within the reactor.

DESCRIPTION OF THE PREFERRED EMBODIMENTS

Figure 1:
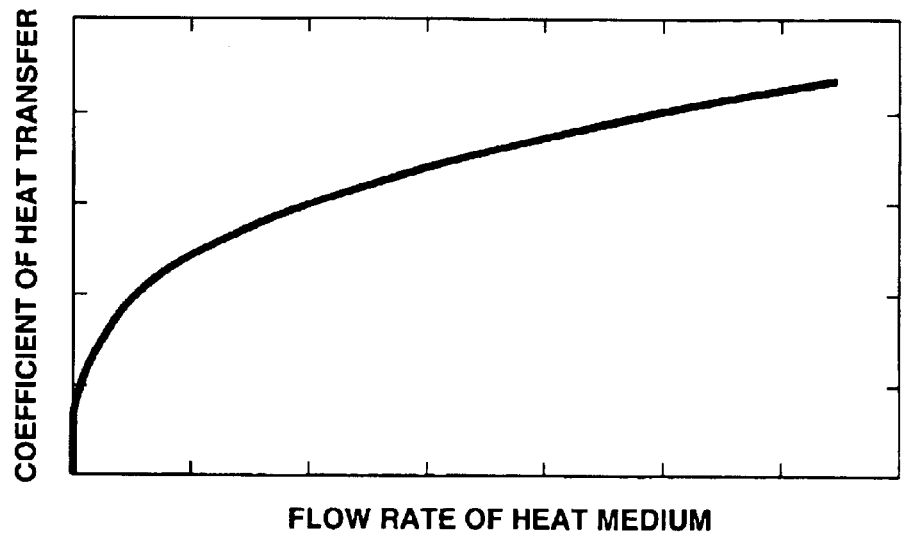
FIG. 1 is a diagram of the coefficient of heat transfer versus the flow rate of a heat medium.

The process for preparing oganohalosilanes according to the present invention involves the steps of charging a reactor with a contact mass containing metallic silicon and a copper catalyst, and introducing an organohalide-containing gas feed into the reactor to effect reaction to form organohalosilanes represented by the formula (1):

$$R_nH_mSiX_{(4-n-m)} \quad (1)$$

wherein R is a monovalent hydrocarbon group, X is a halogen atom, n is an integer of 1 to 3, m is an integer of 0 to 2, and the sum of n+m is an integer of 1 to 3.

In formula (1), the monovalent hydrocarbon groups represented by R are preferably of 1 to 6 carbon atoms, for example, alkyl, alkenyl and aryl groups. Of these, alkyl groups such as methyl, ethyl and propyl and phenyl are preferred, with methyl being most preferred. Preferably, the letter n is 2, m is 0, and n+m=2. The halogen atoms represented by X include chlorine, bromine and fluorine, with chlorine being preferred.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 5 to 150 µm, corresponding to 50% of the weight-base cumulative size distribution curve on sieving, in order that the metallic silicon powder have good fluidity.

The copper catalyst used herein may be selected from various forms of copper including elemental copper (or metallic copper) such as powdered copper and stamped copper, and copper compounds such as cuprous oxide, cupric oxide, and copper halides. Any of promoters such as zinc, tin, antimony, aluminum, phosphorus and arsenic may be used as the co-catalyst. The co-catalyst may be used alone or in the form of an alloy with copper. Examples of the co-catalyst which is used alone include metallic zinc, zinc-copper alloys, zinc compounds such as zinc chloride, zinc oxide, and zinc acetate, metallic tin, tin-copper alloys, tin compounds such as tin chloride and tin oxide, metallic antimony, antimony compounds such as antimony chloride and antimony oxide, metallic aluminum, aluminum compounds such as aluminum chloride and aluminum oxide, metallic phosphorus, inorganic phosphorus compounds such as phosphorus trichloride and phosphorus oxide, and organic phosphorus compounds such as trimethylphosphine, triphenylphosphine and monoalkylphosphines. Exemplary combinations of copper catalyst with co-catalyst include copper alloys like Cu—Zn, Cu—Sn, and Cu—Zn—Sn (or Sb or As). Of these, metallic zinc, zinc compounds, metallic tin, tin compounds, metallic antimony, antimony compounds, metallic aluminum, aluminum compounds, metallic phosphorus, and phosphorus compounds (excluding phosphonium compounds) are preferred.

The copper catalyst may be admitted into the reactor alone or in combination with the co-catalyst, along with metallic silicon powder. The amount of the copper catalyst blended is an effective amount, preferably about 0.1 to 10 parts, and more preferably about 2 to 8 parts by weight per 100 parts by weight of the metallic silicon powder. The amount of the co-catalyst blended is an effective amount, preferably about 0.0001 to 3 parts, and more preferably about 0.001 to 1 part by weight per 100 parts by weight of the metallic silicon powder. For example, zinc is preferably used in an amount of 0.01 to 2 pbw, especially 0.05 to 1 pbw per 100 pbw of the metallic silicon powder. Tin, antimony and arsenic are preferably used in a single or total amount of 0.001 to 0.05 pbw, especially 0.005 to 0.01 pbw per 100 pbw of the metallic silicon powder. Aluminum is preferably used in an amount of 0.001 to 1 pbw, especially 0.005 to 0.5 pbw per 100 pbw of the metallic silicon powder. Phosphorus is preferably used in an amount of 0.001 to 2 pbw, especially 0.005 to 1 pbw per 100 pbw of the metallic silicon powder. When zinc compounds or other compounds are used, they are preferably added in such amounts as to give the above-described amount of metal. These co-catalysts may be used in admixture of two or more.

The organohalide to be reacted with metallic silicon to form organohalosilanes of the formula (1) is preferably selected from organohalides having 1 to 6 carbon atoms. Suitable organohalides include methyl chloride, ethyl chloride, propyl chloride, methyl bromide, ethyl bromide, benzene chloride and benzene bromide. Of these, methyl chloride and benzene chloride are preferable in the industry. Methyl chloride is most useful because organohalosilanes, typically dimethyldichlorosilane, produced therefrom find a wide variety of applications as the raw material for many silicone resins.

The organohalide is previously heated and gasified before it is admitted into the reactor. The organohalide gas may be fed alone or combined with an inert gas in a sufficient amount to fluidize the contact mass, the fluidizing amount being determined as appropriate from the diameter of the reactor and the superficial velocity. In the practice of the invention, the feed rate of organohalide gas is adjusted to manipulate the partial pressure of organohalide gas for thereby maintaining the temperature within the reactor at a desired level.

In the step of heating the contact mass or imparting catalytic activity to the contact mass, an inert gas is used for fluidizing the contact mass in the reactor. The flow velocity of the inert gas fed for fluidization is at least the minimum fluidization velocity of the contact mass, and preferably about 5 times the minimum fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas and the organohalide as will be described later.

After the contact mass is given catalytic activity as mentioned above, the organohalide is introduced into the reactor where gas-solid catalytic reaction takes place between the organohalide and metallic silicon to form organohalosilanes.

According to the invention, the reactor interior is maintained at an appropriate temperature by manipulating the partial pressure of organohalide gas in the gas feed to the reactor to control the amount of heat generated by reaction. The organohalide partial pressure can be manipulated by adjusting the feed rate of the organohalide, which can be, in turn, adjusted by means of a regulating valve in an organohalide supply line. Then the feed rate can be adjusted with a very high precision.

More particularly, methylchlorosilanes, for example, are industrially produced using a fluidized bed reactor. A certain flow velocity must be established in the fluidized bed in order to maintain an effective fluidized state therein. The flow velocity through the fluidized bed becomes the factor to dictate the fluidized state, the coefficient of heat transfer and a fraction of powder scattered. Thus the fluidizing gas must be introduced at such a velocity as to provide an effective fluidization and a high coefficient of heat transfer and to prevent excessive scattering of powder. Such a flow velocity can be established by admixing methyl chloride and an inert gas in the fluidizing gas. Further, in order to maintain the temperature within the reactor at a desired value and keep the flow velocity and superficial velocity through the fluidized bed constant, a method of introducing an amount of methyl chloride necessary to maintain the temperature within the reactor and changing the feed rate of inert gas, so as to make constant the overall volume flow rate may be employed.

In the industrial production of methylchlorosilanes, unreacted methyl chloride and the inert gas are recycled. The product gas exiting the reactor contains methylchlorosilanes, unreacted methyl chloride and inert gas. After methylchlorosilanes are removed from the product gas, the remaining gas (methyl chloride and inert gas) is introduced into the reactor again. It is possible in this case that once the methyl chloride is separated from the inert gas, the partial pressure of methyl chloride is adjusted, and the methyl chloride is then fed so as to enable temperature control within the reactor and along with the inert gas to provide a necessary flow velocity.

However, the procedure of once separating the methyl chloride from the inert gas and subsequently remixing them is inefficient. It is thus recommended from the economic aspect that after methylchlorosilanes are removed from the product gas exiting the reactor, the remaining gas (containing methyl chloride and inert gas) be introduced into the reactor again as the recycle gas without further separation.

In this event, to maintain an appropriate temperature within the reactor, fresh methyl chloride is admixed with the recycle gas containing methyl chloride and inert gas for manipulating the partial pressure of methyl chloride in the gas mixture. The partial pressure of methyl chloride can be manipulated by adjusting the feed rate of fresh methyl chloride and the feed rate of the recycle gas.

More particularly, by increasing the ratio of fresh methyl chloride/recycle gas, the partial pressure of methyl chloride in the fluidizing gas is increased whereby the amount of heat generation can be increased for elevating the temperature within the reactor. Inversely, by reducing the ratio of fresh methyl chloride/recycle gas, the partial pressure of methyl chloride in the fluidizing gas is reduced whereby the amount of heat generation can be reduced for lowering the temperature within the reactor. In the practice of the invention, it is preferred to keep the range of fluctuation of the reactor internal temperature within ±2° C., and especially within ±1° C.

Since the ratio of fresh methyl chloride/recycle gas is quickly changed by manipulation of a regulating valve in a fresh methyl chloride supply line, adjustment can be completed in a brief time as compared with the manipulation of the temperature or flow rate of heat medium, so that the control of reaction temperature can be performed with a very high precision. The manipulation of a regulating valve may be done manually, but preferably by an automatic control unit. The automatic control unit is programmed so that upon receipt of an input indicating the reactor internal temperature, the unit delivers an output indicating the degree of opening of the regulating valve. The automatic control algorithm is not particularly limited as long as the reactor internal temperature can be properly controlled. PID control is often employed.

Figure 2:
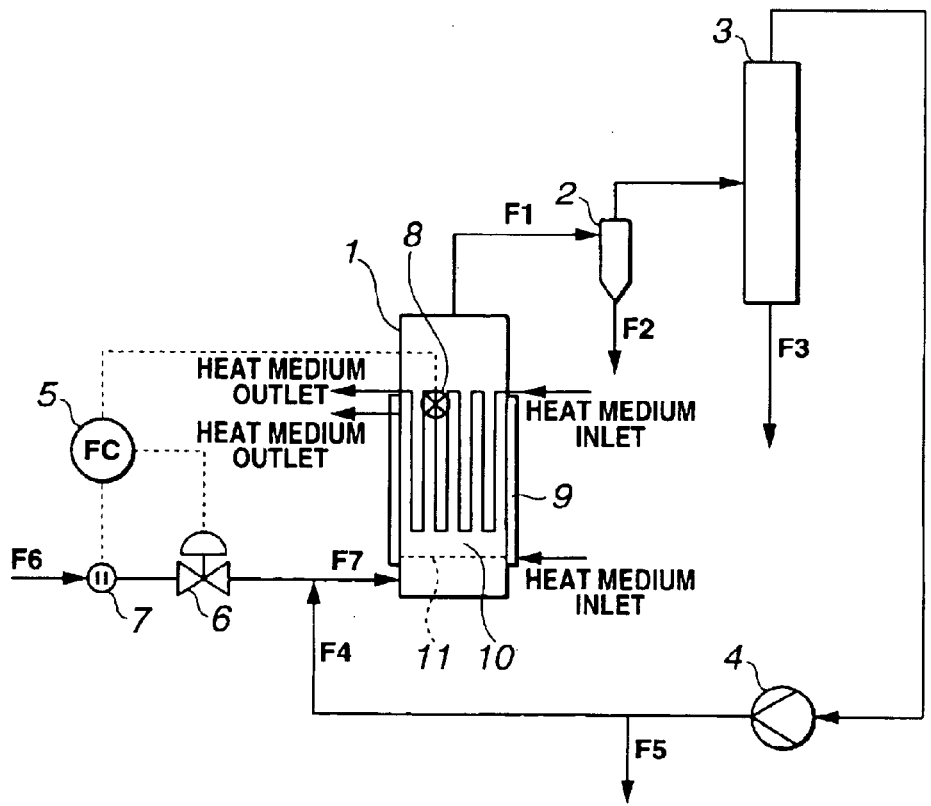
FIG. 2 schematically illustrates an organohalosilane producing system according to one embodiment of the invention.

Referring to FIG. 2, a specific control mode of maintaining appropriate the temperature within the reactor using the method of the present invention is now described.

The system shown in FIG. 2 includes a fluidized bed reactor 1, a cyclone 2, a separator 3, a compressor 4, an automatic control unit 5, a regulating valve 6, a flow meter 7, a temperature sensor 8 disposed in a fluidized bed formed in the reactor 1, a jacket 9, an inner coil 10, and a dispersing plate 11. Also illustrated are a product gas F1, fines F2, an organohalosilane-containing fluid F3, a recycle gas F4, a purge line F5, fresh organohalide F6, and a fluidizing gas F7.

In the illustrated system, the temperature within the reactor 1 is measured by the sensor 8. The measurement by the sensor 8 is delivered as an input to the automatic control unit 5. Upon receipt of the measurement input, the automatic control unit 5 operates in accordance with the preset algorithm and delivers an output signal to the regulating valve 6 to manipulate the degree of opening of the valve. At this point, the flow rate of fresh organohalide gas F6 is measured by the flow meter 7. The fresh organohalide gas whose flow rate is adjusted by the regulating valve 6 is admixed with the recycle gas F4 containing organohalide and inert gas, and the mixture fed as the fluidizing gas F7 to the fluidized bed reactor 1. The partial pressure of organohalide gas in the fluidizing gas becomes higher with the increasing degree of opening of the regulator valve 6, and vice versa. Accordingly, the temperature within the reactor is controlled and maintained at an appropriate level.

The arrangement of the dispersing plate 11 and the inner coil 10 within the reactor 1 and the jacket 9 around the reactor 1 enables heating and cooling. The temperature of heat medium through the inner coil 10 and jacket 9 should not be too low because at too low a temperature, high-boiling products and metal chlorides will condense on the heat transfer surface. Since the quantity of cooling is determined by the flow rate and temperature of heat medium, they are manually or automatically set appropriate in accordance with the reaction rate. In case the temperature within the reactor is beyond the range where adjustment can be made in terms of only the partial pressure of organohalide in the fluidizing gas, further adjustment is made by settings of the flow rate and temperature of heat medium.

The product gas F1 exiting the reactor 1 enters the cyclone 2 where fines F2 are collected and then the separator 3 where low-boiling components containing organohalide and inert gas are separated from the product F3 containing organohalosilanes. The organohalide and inert gas-containing gas serving as the recycle gas is pressure-boosted in the compressor 4, after which a portion F5 thereof is purged and the other portion is admixed with fresh organohalide and circulated to the reactor 1 for reuse.

There has been described an exemplary procedure of manipulating the partial pressure of organohalide in the fluidizing gas. Whatever procedure other than the above-described is employed, by manipulating the partial pressure of organohalide in the fluidizing gas, the temperature within the reactor can be controlled with a high precision to maintain the reaction temperature. Any gas like nitrogen, helium or argon gas may be used as the inert gas insofar as the reaction within the system is not affected thereby. Nitrogen gas is preferable from the economic standpoint. The recycle gas contains low-boiling hydrocarbons such as methane, ethane and propane that form in the reactor, in addition to the inert gas and organohalide. It is not necessarily required to remove such low-boiling components because they have no substantial impact on the reaction. The method of the invention may be practiced in a fluidized bed reactor, stirred bed reactor or fixed bed reactor.

In the practice of the invention, the partial pressure of organohalide in the fluidizing gas F7 is preferably in a range of 0.01 to 0.50 MPa, especially 0.03 to 0.30 MPa. The concentration of organohalide in the fluidizing gas is preferably in a range of 10 to 90% by weight, especially 20 to 80% by weight. The temperature within the fluidized bed is in a range of about 230 to 600° C., and for the production of methylchlorosilanes, in a range of about 250 to 350° C. The method of the invention ensures that the temperature within the reactor is maintained at the preset temperature in the above-specified range with fluctuations of ±2° C.

EXAMPLE

Examples of the invention are given below by way of illustration and not by way of limitation.

Example 1

Figure 3:
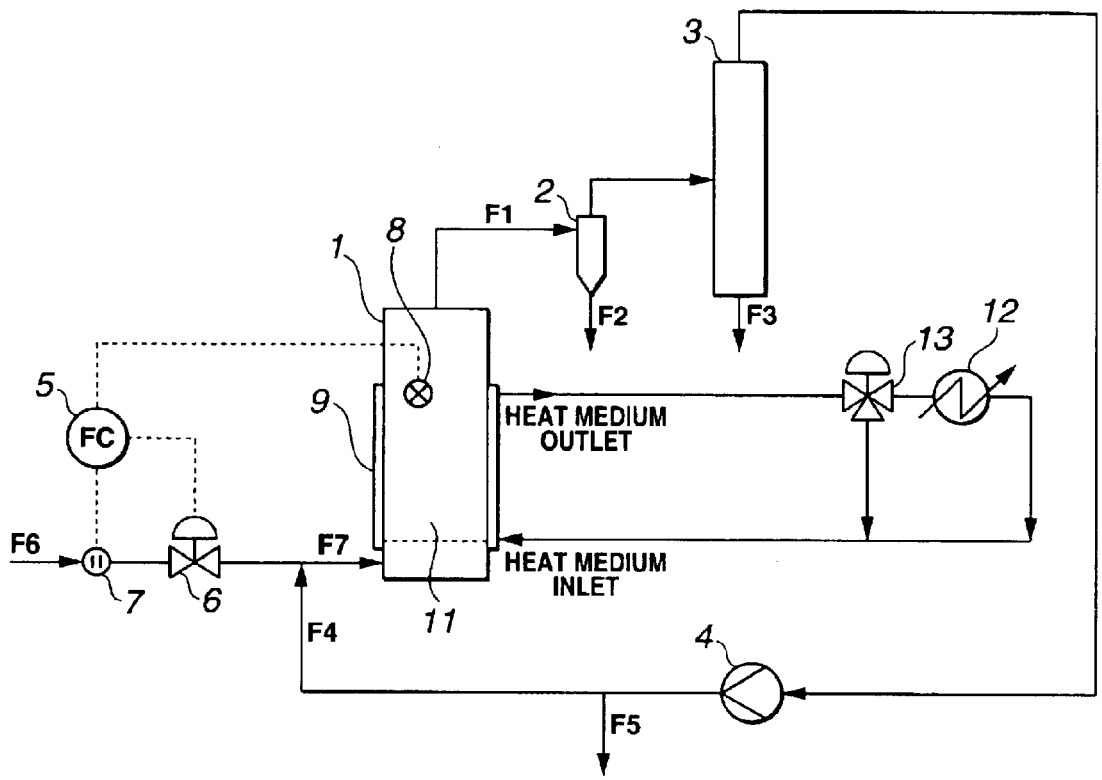
FIG. 3 schematically illustrates an exemplary methylchlorosilane producing system according to the invention.

Reaction Temperature Control by Manipulation of Methyl Chloride Partial Pressure Using a system shown in FIG. 3 including a fluidized bed reactor (inner diameter 33 cm, height 500 cm) equipped with a heat medium circulating jacket, a dispersing plate and a temperature sensor, methylchlorosilanes were prepared.

While nitrogen gas was flowed through the reactor at a linear velocity in column of 2 cm/s, 300 kg of a contact mass containing metallic silicon and a catalytic amount of copper, zinc and aluminum was admitted into the reactor. Then nitrogen gas was introduced so as to provide a linear velocity of 18 cm/s, and the internal temperature of the reactor was raised to 285° C. After the temperature rise, a fluidizing gas containing methyl chloride was introduced to initiate reaction. At this point, the automatic control of the temperature within the reactor was performed such that the partial pressure of methyl chloride in the fluidizing gas was manipulated to maintain the temperature within the reactor at a constant level of 305° C. The fluidizing gas was obtained by admixing fresh methyl chloride gas with the recycle gas which was obtained by removing methylchlorosilanes from the product gas exiting the reactor. By manipulating the mixing ratio, the partial pressure of methyl chloride was changed. The gas feed was maintained at a linear velocity of 18 cm/s.

Once the reaction is initiated by introducing methyl chloride into the loaded reactor, heat generates due to the reaction. Thus, at the same time as methyl chloride was introduced, the heat medium at a lower temperature than the reactor internal temperature was passed through the jacket for cooling.

Referring to FIG. 3, the method of controlling the reactor internal temperature is described in detail. In FIG. 3, the same components as in FIG. 2 are designated by like numerals. In the system of FIG. 3, a heat medium heating/cooling unit 12 and a heat medium flow rate regulating valve 13 are provided in a heat medium circulation line coupled to the jacket 9. The temperature within the reactor 1 was measured by the sensor 8, whose reading was delivered to the automatic control unit 5 as an input signal. Upon receipt of the input, the automatic control unit 5 operated in accordance with the PID control algorithm and delivered an output signal to the flow rate regulating valve 6 for fresh methyl chloride. Fresh methyl chloride was admixed with the recycle gas which was obtained by removing methylchlorosilanes from the product gas exiting the reactor, after which the mixture was fed to the reactor. By changing the partial pressure of methyl chloride by this procedure, the temperature within the reactor was maintained constant. The temperature of the heat medium introduced into the jacket for cooling purpose was manually adjusted once a day or so to provide a substantially constant quantity of cooling while the overall flow rate was kept constant.

The reaction was continued for 420 hours while the contact mass was continuously made up so that the amount of the contact mass in the reactor and the concentrations of copper, zinc and tin remained constant. The partial pressure and concentration of methyl chloride at the reactor inlet changed in accordance with the temperature control, the partial pressure shifting in a range of 0.067 to 0.121 MPa and the concentration shifting in a range of 38.2 to 61.5% by weight. At this point, the temperature within the reactor exhibited a minimized range of fluctuation, and was maintained at the desired level within ±1° C. The average formation rate (methylchlorosilane formation rate per unit time and per metallic silicon-weight) was 136 (kg-silane/ h·t-Si). The compositions of dimethyldichlorosilane and methyltrichlorosilane in crude methylchlorosilanes were 88.2 wt % and 4.5 wt %, respectively.

Figure 4:
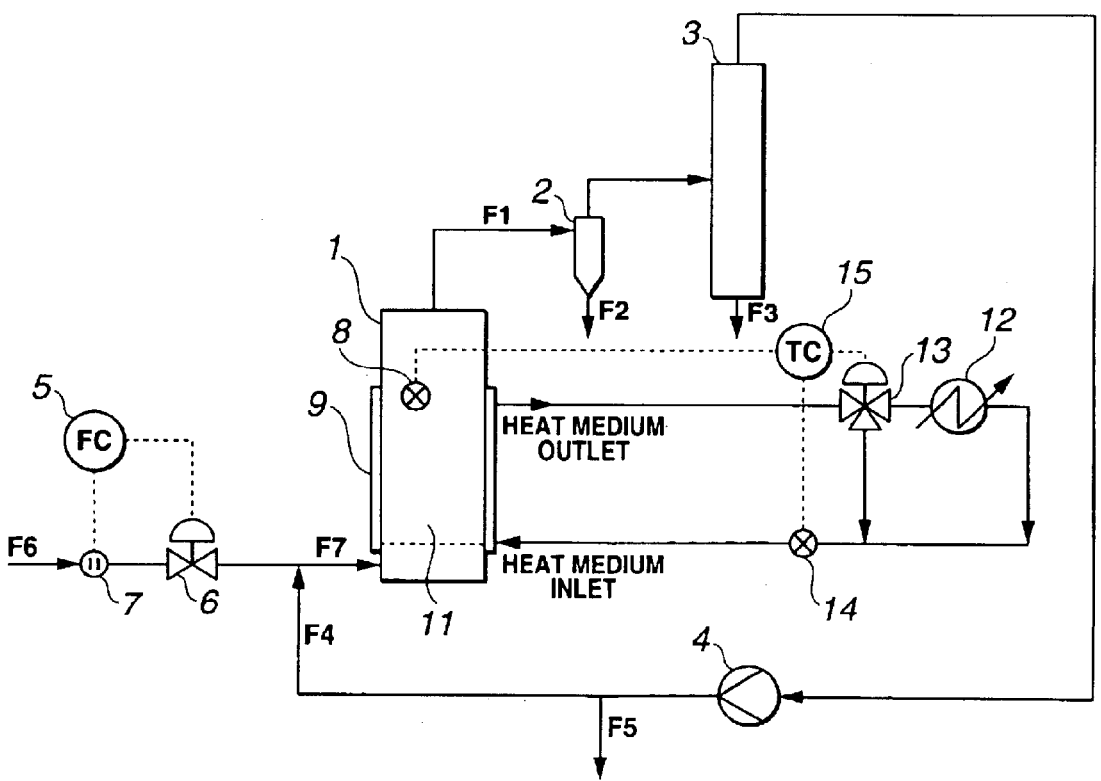
FIG. 4 schematically illustrates an exemplary methylchlorosilane producing system used in Comparative Example.

Comparative Example 1
Reaction Temperature Control by Manipulation of Heat Medium Temperature Using a system shown in FIG. 4 including a fluidized bed reactor (inner diameter 33 cm, height 500 cm) equipped with a heat medium circulating jacket, a dispersing plate and a temperature sensor, methylchlorosilanes were prepared.

While nitrogen gas was flowed through the reactor at a linear velocity in column of 2 cm/s, 300 kg of a contact mass containing metallic silicon and a catalytic amount of copper, zinc and aluminum was admitted into the reactor. Then nitrogen gas was introduced so as to provide a linear velocity of 18 cm/s, and the internal temperature of the reactor was raised to 285° C. After the temperature rise, a fluidizing gas containing methyl chloride was introduced to initiate reaction. The fluidizing gas was obtained by admixing fresh methyl chloride gas with the recycle gas which was obtained by removing methylchlorosilanes from the product gas exiting the reactor. The gas feed was maintained at a linear velocity of 18 cm/s. Fresh methyl chloride was fed at a constant rate of 32 kg/h. At this point, the automatic control of the temperature within the reactor was performed such that the temperature of heat medium introduced into the jacket was manipulated to maintain the temperature within the reactor at a constant level of 305° C.

Referring to FIG. 4, the method of controlling the reactor internal temperature is described in detail. In FIG. 4, the same components as in FIGS. 2 and 3 are designated by like numerals. In the system of FIG. 4, a temperature sensor 14 and an automatic control unit 15 are provided in a heat medium circulation line coupled to the jacket 9. The temperature within the reactor 1 was measured by the sensor 8, whose reading was delivered to the automatic control unit 15 as an input signal. Upon receipt of the input, the automatic control unit 15 operated in accordance with the PID control algorithm and delivered an output signal to a flow rate regulating valve 13 for heat medium. The actuated valve adjusted the flow rate of heat medium through a heat medium cooler 12 to change the temperature of heat medium through the jacket 9. This example attempted to maintain the temperature within the reactor constant by adjusting the temperature of heat medium through the jacket 9 in this way. The temperature of heat medium at the jacket inlet shifted in a range of 283 to 305° C. The overall flow rate of heat medium was kept constant.

The reaction was continued for 409 hours while the contact mass was continuously made up so that the amount of the contact mass in the reactor and the concentrations of copper, zinc and tin remained constant. The partial pressure of methyl chloride at the reactor inlet shifted in a range of 0.094 to 0.119 MPa and the concentration of methyl chloride shifted in a range of 48.0 to 61.7% by weight. At this point, the temperature within the reactor exhibited a wide range of fluctuation and varied within ±5° C. The average formation rate (methylchlorosilane formation rate per unit time and per metallic silicon weight) was 132 (kg-silane/h·t-Si). The compositions of dimethyldichlorosilane and methyltrichlorosilane in crude methylchlorosilanes were 85.9 wt % and 5.6 wt %, respectively.

From the results reported above, the reaction temperature control based on manipulation of the partial pressure of methyl chloride gas provides a minimize range of fluctuation of reaction temperature as compared with the control by way of heat medium temperature, and thus ensures the formation of dimethyldichlorosilane in higher yields.

The inventive method enables to control the reactor internal temperature in a highly precise manner by manipulating the partial pressure of organohalide gas in the fluidizing gas. Then, from the contact mass which changes its reactivity at all times, organohalosilanes can be produced in a safe and inexpensive manner, with the productivity of useful silane being high.

Japanese Patent Application No. 2002-338840 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing oganohalosilanes comprising the steps of charging a reactor with a contact mass containing metallic silicon particles and a copper catalyst, and introducing an organohalide-containing gas feed into the reactor to effect reaction to form organohalosilanes, characterized in that the partial pressure of organohalide gas in the gas feed is manipulated so as to keep a substantially constant temperature within the reactor.

2. The process of claim 1 wherein the partial pressure of organohalide gas in the gas feed is manipulated by adjusting the feed rate of organohalide gas in the gas feed to the reactor.

3. The process of claim 1 wherein the gas feed contains the organohalide gas and an inert gas, and the inert gas and unreacted organohalide gas exiting the reactor are recycled to the reactor.

4. The process of claim 3 wherein the gas feed is maintained at a constant flow velocity through the reactor, and the partial pressure of organohalide gas in the gas feed is manipulated by adjusting the ratio of the recycle gas to fresh organohalide gas.

5. The process of claim 3 wherein the inert gas is nitrogen gas.

6. The process of claim 1 wherein the gas feed to the reactor contains the organohalide gas in a concentration of 15 to 70% by weight.

* * * * *